United States Patent [19]

Sakurai et al.

[11] Patent Number: 5,286,883

[45] Date of Patent: Feb. 15, 1994

[54] (3R,5S)-3,5,6-TRIHYDROXYHEXANOIC ACID DERIVATIVE AND PRODUCTION METHOD THEREOF

[75] Inventors: Kazutoshi Sakurai; Shigeru Mitsuhashi; Hidenori Kumobayashi, all of Tokyo, Japan

[73] Assignee: Takasago International Corporation, Tokyo, Japan

[21] Appl. No.: 976,498

[22] Filed: Nov. 13, 1992

[30] Foreign Application Priority Data

Aug. 13, 1992 [JP] Japan .................................. 4-216070

[51] Int. Cl.$^5$ .......................................... C07D 309/12
[52] U.S. Cl. .................................................... 549/420
[58] Field of Search ......................................... 549/420

[56] References Cited

U.S. PATENT DOCUMENTS

| | | | |
|---|---|---|---|
| 4,248,889 | 2/1981 | Oka et al. | 560/56 |
| 4,691,037 | 9/1987 | Yoshikawa et al. | 556/18 |
| 4,970,313 | 11/1990 | Wess et al. | 544/335 |
| 4,983,759 | 1/1991 | Inoue et al. | 549/654 |
| 4,994,602 | 2/1991 | Seido et al. | 560/186 |
| 5,003,080 | 3/1991 | Butler et al. | 548/517 |

FOREIGN PATENT DOCUMENTS 0244364 11/1987 European Pat. Off. .

OTHER PUBLICATIONS

K. Prasad et al., *Tetrahedron Letters*, vol. 25, No. 32, pp. 3391–3394, 1984.
J. R. Prous, *Drugs Of The Future*, vol. 12, No. 5, pp. 437–442, 1987.
T. Lee, *Tetrahedron Letters*, vol. 26, No. 41, pp. 4995–4996, 1985.
T. Hanamoto et al., *Tetrahedron Letters*, vol. 29, No. 49, pp. 6467–6470, 1988.
G. Wess et al., *Tetrahedron Letters*, vol. 31, No. 18, pp. 2545–2548, 1990.
K. Prasad et al., *Tetrahedron: Asymmetry*, vol. 1, No. 5, pp. 307–310, 1990.
M. Fukui et al., *Chem. Pharm. Bull.*, vol. 38, No. 10, pp. 2890–2892, 1990.
D. A. Evans et al., *J. Org. Chem.*, vol. 56, No. 2, pp. 741–750, 1991.
K. Chen et al., *Tetrahedron Letters*, vol. 28, No. 2, pp. 155–158, 1987.
K. Chen et al., *Chemistry Letters*, pp. 1923–1926, 1987.
F. G. Kathawala et al., *Helvetica Chimica Acta*, vol. 69, pp. 803–805, 1986.
J. E. Lynch et al., *Tetrahedron Letters*, vol. 28, No. 13, pp. 1385–1388, 1987.
N. Balasubramanian et al., *Journal of Medicinal Chemistry*, vol. 32, No. 9, pp. 2038–2041, 1989.
S. Y. Sit et al., *Journal of Medicinal Chemistry*, vol. 33, No. 11, pp. 2982–2999, 1990.
G. J. McGarvey et al., *J. Org. Chem.*, vol. 51, No. 20, pp. 3913–3915, 1986.
T. Ikariya et al., *J. Chem. Soc., Chem., Commun.*, pp. 922–924, 1985.s.

*Primary Examiner*—Nicky Chan
*Attorney, Agent, or Firm*—Sughrue, Mion, Zinn, Macpeak & Seas

[57] ABSTRACT

A (3R,5S)-3,5,6-trihydroxyhexanoic acid derivative and a process of producing the (3R,5S)-3,5,6-trihydroxyhexanoic acid derivative which comprises the step of enantioselectively hydrogenating an (S)-5,6-dihydroxy-3-oxohexanoic acid derivative with a specific ruthenium-optically active phosphine complex represented as a catalyst are disclosed. The (3R,5S)-3,5,6-trihydroxyhexanoic acid derivative which is a useful compound capable of being easily converted into a lactone moiety, which is the active part of an inhibitor on HMG-CoA reductase, can be easily and efficiently obtained under a mild reaction condition with a high selectivity for the syn-diol form.

1 Claim, No Drawings

(3R,5S)-3,5,6-TRIHYDROXYHEXANOIC ACID DERIVATIVE AND PRODUCTION METHOD THEREOF

FIELD OF THE INVENTION

The present invention relates to a novel compound, (3R,5S)-3,5,6-trihydroxyhexanonic acid derivative useful as an intermediate as synthetic raw materials for medicaments and also to a method of producing the compound.

BACKGROUND OF THE INVENTION

Some of the optically active compounds, (3R,5S)-3,5,6-trihydroxyhexanoic acid derivatives having the specific configuration shown by following formula (1')

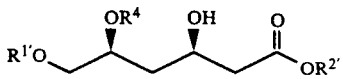
(1')

(wherein $R^{1'}$ and $R^4$ each represents a hydrogen atom or a protective group for a hydroxy group and $R^{2'}$ represents an ester forming group), are already known compounds and it is reported that these compounds can be easily converted into lactone moieties of a chemical structure of compactin, mevinolin, etc., which are given attention as an antihyperlipemia as described in K. Prasad et al., *Tetrahedron Lett.*, Vol. 25, No. 32, 3391-3394(1984). It is considered that the lactone moiety is the active part of an inhibitor on 3-hydroxy-3-methylglutarylcoenzyme A (hereinafter, is referred to as "HMG-CoA") reductase, one of the predominant enzymes taking part in the increase of the concentration of cholesterol, which is the cause of hyperlipemia and many analogs having the lactone moiety have been synthesized [J. R. Prous, *Drugs of the Future*, Vol. 12, No. 5, 437-442(1987)].

Many methods of synthesizing the (3R,5S)-3,5,6-trihydroxyhexanoic acid derivatives shown by foregoing formula (1') have been reported. In these methods, as a method originated in a raw material compound having asymmetric carbon atoms at two portions, there is a method of synthesizing from D-glucose which is a natural optically active compound as described in T. Lee, *Tetrahedron Lett.*, Vol. 26, No. 41, 4995-4996(1985) but the method has a disadvantage that the reaction step up to obtained the desired compound is long.

Also, as a method of simultaneously introducing hydroxy groups at two portions into a syn-diol form, there is a method of obtaining a 3,5-dioxohexanoic acid derivative by reacting an acetoacetic acid derivative and an amide compound and reducing the reaction product using sodium borohydride and an alkoxydialkylborane at a temperature from −70° C. to −78° C. as described in JP-A-1-165547 (the term "JP-A" as used herein means an "unexamined published Japanese patent application") and T. Hanamoto et al., *Tetrahedron Lett.*, Vol. 29, No. 49, 6467-6470(1988) but by the method, a diastereomer only is determined but a desired optically active material can not be obtained.

A method of forming asymmetric carbon atoms at two portions one by one has been most widely utilized and as the methods, following methods (a) to (g) are reported.

(a) A method of obtaining an (S)-5,6-dihydroxy-3-oxohexanoic acid derivative shown by following formula (2')

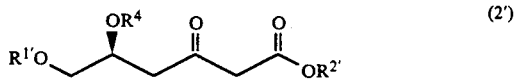
(2')

wherein $R^{1'}$ and $R^4$ each represents a hydrogen atom or a protective group for a hydroxy group and $R^{2'}$ represents an ester forming group, from an (S)-3,4-dihydroxybutanoic acid ester derivative shown by following formula (5)

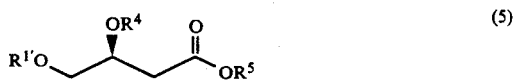
(5)

wherein $R^{1'}$ and $R^4$ have the same meaning as described above and $R^5$ represents a hydrogen atom or an alkyl group, synthesized from L-malic acid, which is a natural material, and diastero-selectively reducing the foregoing hexanoic acid derivative using a reducing agent such as a mixture of sodium borohydrate and a trialkylborane or a mixture of sodium borohydrate and an alkoxydialkylborane under a low temperature condition of about −70° C. [European Patent 0 244 364 A2, U.S. Pat. No. 4,970,313, G. Wess et al., *Tetrahedron Lett.*, Vol. 31, No. 18, 2545-2548(1990), and K. Prasad et al., *Tetrahedron: Asymmetry*, Vol. 1, No. 5, 307-310(1990)].

(b) A method of obtaining the compound shown by foregoing formula (2') by reacting an optically active butyronitrile derivative and an α-haloacetic acid ester in the presence of zinc and diastero-selectively reducing the reaction product as in step (a) described above (U.S. Pat. No. 4,983,759).

(c) A method of synthesizing the compound shown by formula (2') from an optically active 3-hydroxypropionaldehyde derivative and diastero-selectively reducing the synthesized product as in step (a) described above [M. Fukui et al., *Chem. Pharm. Bull.*, Vol. 38, No. 10, 2890-2892(1990)].

(d) A method of synthesizing the compound shown by formula (2') from 3-(3-methoxyphenyl)-2-propen-1-ol and then diastero-selectively reducing the synthesized compound as in step (a) [D. A. Evans et al., *J. Org. Chem.*, Vol. 56, No. 2, 741-750(1991)].

In addition, the diastero-selective reducing reaction of compound shown by formula (2') common to the steps (a) to (d) is also reported in K. Chen et al., *Tetrahedron Lett.*, Vol. 28, No. 2, 155-158(1987), K. Chen et al., *Chemistry Lett.*, 1923-1926(1987), etc. Also, in F. G. Kathawala et al., *Helv. Chim. Acta*, Vol. 69, 803-805(1986), the diastero-selectivities for the compound shown by foregoing formula (1') obtained in the case of using sodium borohydrate and a trialkylborane, the case of using ferrous chloride, the case of using zinc borohydride, etc., for the diastero-selective reducing reaction of the compound shown by formula (2') are compared. Furthermore, it is reported that in the compound shown by formula (1') having an allyl group or a cyano group in place of the hydroxy group at the 6-position, which is an analogous compound to the foregoing compound shown by formula (1'), by applying the diastero-selective reducing reaction to the substrate obtained by carrying out, for example, an asymmetric aldol condensation of the aforesaid compound, and then optically resolving the reaction product, a corresponding optically active 3,5-dihydroxyhexanoic acid derivative can be obtained [J. E. Lynch et al., *Tetrahedron Lett.*, Vol. 28, No. 13, 1385-1388(1987); N. Balasubramanian et al., *J. Med. Chem.*, Vol No. 9, 2038-2041(1989); S. Y. Sit et al., *J. Med. Chem.*, Vol. 33, No. 11, 2982-2999(1990), U.S. Pat. No. 5,003,080].

(e) A method of obtaining the compound shown by formula (2') by reacting the dianion of acetoacetic acid ester with aldehyde and reducing the compound by reacting the compound using sodium borohydrate in absolute ethanol under ice-cooling (U.S. Pat. No. 4,248,889).

(f) A method of obtaining the compound shown by formula (5) by ring-cleaving optically active 1-benzyloxy-2,3-epoxy-4-hydroxybutane and after introducing a protective group to the hydroxy group, oxidizing the product, and synthesizing by carrying out a Reformatsky reaction of the compound of formula (5) using ethyl bromoacetate and zinc [K. Prasad et al., *Tetrahedron Lett.*, Vol. 25, No. 32, 3391-3394(1984)].

(g) A method of reacting a (3R,5R)-5-amino-3-hydroxyhexanoic acid derivative and a specific cyan compound [Na₂Fe(CN)₅NO] using potassium carbonate [G. J. McGarvey et al., *J. Org. Chem.*, Vol. 51, No. 20, 3913-3915(1986)].

However, the above-described methods each has the following defect.

That is, the method (e) is a method of obtaining a racemic modification and a desired optically active substance can not be obtained.

In the method (f), it is difficult to obtain the optically active epoxide which is the raw material, and also the Reformatsky reaction does not have the selectivity for the desired syn-diol form.

In the method (g), it is difficult to obtain the raw material and also the yield for the desired compound is low.

The diastereo-selective reducing reaction which is utilized for methods (a) to (d), which are mostly reported, is a method of inducing an asymmetric point at another portion by utilizing the asymmetric point of one portion and in methods (a) to (d), a desired compound can be obtained with a considerably high syn-diol form selectivity as compared with methods. (e) to (g). However, in methods (a) to (d), the reaction must be carried out under a low temperature condition, whereby a specific equipment is required in the case of synthesizing in an industrial scale, and also in these methods, an expensive reagent is required. Furthermore, in the method (a), L-malic acid which is the raw material is a very expensive compound.

As a method for improving these faults, a method of carrying out an enantioselective hydrogenation of a 4-tert-butoxyacetoacetic acid ester, which can be synthesized at a low cost, as a raw material using a ruthenium-optically active phosphine complex as a catalyst to form an (S)-4-tert-butoxy-3-hydroxybutyric acid ester, reacting the butyric acid ester thus obtained and the lithium enolate of an acetic acid ester to provide an (S)-6-tert-butoxy-5-hydroxy-3-oxohexanoic acid ester, and obtaining the desired compound shown by formula (1') by diastereo-selectively enantioselectively hydrogenating the product thus obtained under a mild temperature condition using a ruthenium-optically active phosphine complex as a catalyst is disclosed in U.S. Pat. No. 994,602.

However, although the method can overcome the foregoing defects in the points of the raw material and the reaction condition, the method is not sufficiently satisfactory in the point that the diastereo-selectivity of the hydroxy group at the 3-position of the compound of formula (1') obtained is not so high as from 60% d.e. to 82% d.e.

In addition, in the foregoing methods, in the methods of carrying out the diastereo-selective reaction, R⁴ of the compound shown by formula (2') is a hydrogen atom in all cases. Accordingly, R⁴ of the compound shown by formula (1') obtained is also a hydrogen atom. In other methods, the compounds shown by formula (1') wherein R⁴ is a hydrogen atom or a protective group for a hydroxy group are synthesized but the protective groups for the hydroxy group practically disclosed are a 3-substituted silyl group and a phenylaminocarbonyl group only, which are reluctant to deprotect, from the reasons of requiring a very expensive reagent and a severe reaction condition.

Thus, the development of a method of simply and efficiently obtaining a (3R,5S)-3,5,6-trihydroxyhexanoic acid derivative the hydroxy group at the 5-position of which can be easily deprotected has been desired.

SUMMARY OF THE INVENTION

As the result of various investigations under such a circumstance, the inventors have discovered that a novel compound, an (S)-5,6-dihydroxy-3-oxohexanoic acid derivative the hydroxy group at the 5-position of which is protected with a tetrahydropyranyl group is obtained and by enantio-selectively asymmetrically hydrogenating the foregoing compound using a specific ruthenium-optically active phosphine complex as a catalyst, a novel compound, a (3R,5S)-3,5,6-trihydroxyhexanoic acid derivative the hydroxy group at the 5-position of which is protected with the tetrahydropyranyl group, which is useful as an intermediate as a synthesis raw material for a medicament, can be easily and efficiently obtained under a mild reaction condition, at a low cost and at a high stereoselectivity of 99.4:0.6 in the formation ratio of the syn-diol form:the anti-diol form and have accomplished the present invention based on the discovery.

That is, according to one aspect of the present invention, there is provided a (3R,5S)-3,5,6-trihydroxyhexanoic acid derivative represented by formula (1)

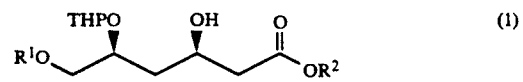

wherein R¹ represents a tert-butyl group or a benzyl group; R² represents a lower alkyl group; and THP represents a tetrahydropyranyl group.

Furthermore, according to another aspect of the present invention, there is provided a process of producing a (3R,5S)-3,5,6-trihydroxyhexanoic acid derivative represented by the formula (1) described above, which comprises the step of enantioselectively hydrogenating an (S)-5,6-dihydroxy-3-oxohexanoic acid derivative represented by formula (2)

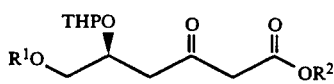

(2)

wherein $R^1$, $R^2$, and THP have the same meaning as described above; with a ruthenium-optically active phosphine complex represented by formula (3) as a catalyst:

(3)

wherein $R^3$—BINAP represents a tertiary phosphine represented by formula (4)

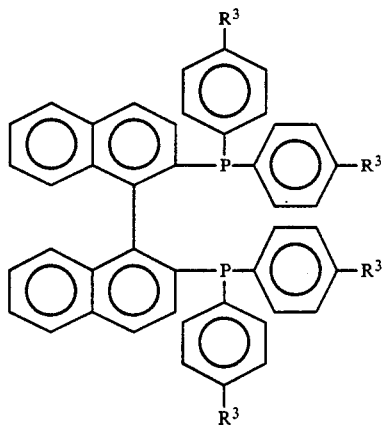

(4)

$R^3$ represents a hydrogen atom or a lower alkyl group; and X represents a chlorine atom or a bromine atom.

DETAILED DESCRIPTION OF THE INVENTION

In the present invention, the term "lower alkyl group" means a straight chain or branched alkyl group having from 1 to 4 carbon atoms.

In the compound of formula (1), $R^2$ preferably is an ethyl group and tert-butyl group.

The (S)-5,6-dihydroxy-3-oxohexanoic acid derivative shown by formula (2) being used in the production method of the present invention as the raw material is a novel compound having a main feature that the hydroxy group at the 5-position is protected with a tetrahydropyranyl group, is inexpensive as compared with the conventional compound protected with a 3-substituted silyl group or a phenylaminocarbonyl group, and also is excellent in the syn-diol form selectivity in the case of producing the (3R,5S)-3,5,6-trihydroxyhexanoic acid derivative shown by formula (1) by the production method of the present invention. Furthermore, when it is necessary to deprotect the tetrahydropyranyl group, it can be easily deprotected under an acid condition, whereby the foregoing derivative of formula (1) can be converted into the original alcohol.

The compound shown by formula (2) can be obtained easily at a low cost and at a high optical purity by, for example, synthesizing the compound according to the following reaction formulae applied with the method described in U.S. Pat. No. 4,994,602:

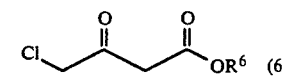
(6)

(A) | $R^1$—OH (7)

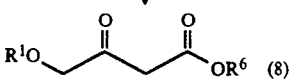
(8)

(B) | Ruthenium-optically active phosphine complex

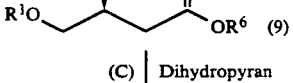
(9)

(C) | Dihydropyran

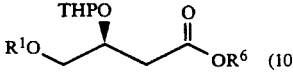
(10)

(D) | Two carbon atoms increased

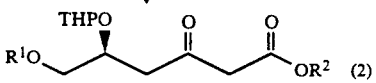
(2)

(In the above formulae, $R^1$, $R^2$, and THP have the same meaning as described above and $R^6$ represents a lower alkyl group).

That is, (A) by reacting the easily commercial available 4-chloroacetoacetic acid ester shown by formula (6) and the alcohol shown by formula (7) by the method described in D. Seebach et al., Synthesis, 37–40(1986), the compound shown by formula (8) is obtained;

(B) then, by enantioselectively hydrogenating the compound of formula (8) using a ruthenium-optically active phosphine complex; Ru[(R)-$R^3$-BINAP]-(O$_2$CR$^7$)$_2$ (wherein $R^3$-BINAP has the same meaning as described above and $R^7$ represents a lower alkyl group or a trifluoromethyl group) obtained by the method described in U.S. Pat. No. 4,739,084 or the ruthenium-optically active phosphine complex shown by foregoing formula (3) being used in the present invention as a catalyst according to the method described in U.S. Pat. No. 4,933,482, the (S)-3,4-dihydroxybutanoic acid ester derivative shown by formula (9) is obtained;

(C) by reacting the compound shown by formula (9) and dihydropyran, the compound of formula (10) wherein the hydroxy group at the 3-position is protected with a tetrahydropyranyl group is obtained; and (D) after reacting the compound of formula (10) and the lithium enolate of an acetic acid ester by the method described in U.S. Pat. No. 4,994,602 or after hydrolyzing the compound of formula (10) with an alkali such as sodium hydroxide, the reaction product or the hydrolyzed product is reacted with a malonic acid derivative such as potassium tert-butyl malonate, potassium ethyl malonate, etc., by applying the method described in U.S. Pat. No. 5,003,080 to increase two carbon atoms, whereby the compound shown by formula (2) is obtained.

The ruthenium-optically active phosphine complex shown by formula (3) being used in the present invention can be obtained by the method described in U.S. Pat. No. 4,691,037 or T. Ikariya et al., *J. Chem. Soc., Chem. Commun.*, 922-924(1985).

That is, the complex shown by formula (3) is produced by reacting under heating [RuX$_2$(COD)]$_m$ (wherein m represents a natural number) obtained by reacting ruthenium halide (wherein the halogen is a chlorine atom or a bromine atom) and cyclooctа-1,5-diene (hereinafter, is referred to as "COD") in ethanol and (R)-R$^3$-BINAP in a solvent such as toluene, ethanol, etc., in the presence of triethylamine.

Specific examples of the ruthenium-optically active phosphine complex shown by formula (3) are as follows:

Ru$_2$Cl$_4$[(R)—BINAP]$_2$N(CH$_2$CH$_3$)$_3$ (wherein BINAP means 2,2'-bis(diphenylphosphino)-1,1'-binaphthyl), Ru$_2$Cl$_4$[(R)-Tol-BINAP]$_2$N(CH$_2$CH$_3$)$_3$ (wherein Tol-BINAP means 2,2'-bis(di-p-tolylphosphino)-1,1'-binaphthyl), Ru$_2$Cl$_4$[(R)-t-Bu-BINAP]$_2$N(CH$_2$CH$_3$)$_3$ (wherein t-Bu-BINAP means 2,2'-bis(di-p-tert-butylphenylphosphino)-1,1'-binaphthyl), Ru$_2$Br$_4$[(R)-BINAP]$_2$N(CH$_2$CH$_3$)$_3$, Ru$_2$Br$_4$[(R)-Tol-BINAP]$_2$N(CH$_2$CH$_3$)$_3$, and Ru$_2$Br$_4$[(R)-t-Bu-BINAP]$_2$N(CH$_2$CH$_3$)$_3$.

The production method of the present invention is as follows.

That is, the (S)-5,6-dihydroxy-3-oxohexanoic acid derivative shown by formula (2) is dissolved in an alcohol such as methanol, ethanol, iso-propanol, tert-butyl alcohol, etc., the ruthenium-optically active phosphine complex shown by formula (3) is added to the solution in an amount of from 0.0001 to 0.002 mol, and preferably from 0.0001 to 0.001 mol, per mol of the compound of formula (2), the hydrogenation is carried out under a hydrogen pressure of from 10 to 120 kg/cm$^2$, and preferably from 20 to 50 kg/cm$^2$ and at a reaction temperature of from 25° to 100° C., and preferably from 30° to 50° C. The solvent was removed by distillation, and the residue formed is purified by silica gel column chromatography to provide the desired (3R,5S)-3,5,6-trihydroxyhexanoic acid derivative shown by formula (1).

The (3R,5S)-3,5,6-trihydroxyhexanoic acid derivative shown by formula (1) thus obtained is a novel compound wherein the hydroxy group at the 5-position is protected with a tetrahydropyranyl group. Also, according to the production method of the present invention, the compound of formula (1) can be obtained easily at a low cost and with a high syn-diol form selectivity.

Also, the compound of formula (1) is excellent in the point that when it is necessary to deprotect the tetrahydropyranyl group in the case of using the compound as a raw material for synthesizing a medicament, the group can be easily deprotected.

In the method of the present invention, it sometimes happens that the compound wherein the hydroxy group at the 5-position is deprotected is by-produced in the step of the purification but the formation of such a compound gives no influence on the foregoing syn-diol form selectivity.

Also, by carrying out the reaction shown below according to the method described, e.g., in U.S. Pat. No. 4,970,313, the isopropylidene acetal, wherein the hydroxy groups at the 3-position and the 5-position are simultaneously protected, shown by formula (12) described below is obtained. The compound can be utilized by the synthesis of the active moiety of an inhibitor on HMG-CoA reductase, but in this case, the compound of formula (1) can be used for the reaction without releasing the tetrahydropyranyl group and also when the compound wherein the hydroxy group at the 5-position is deprotected is by-produced together with the compound shown by formula (1), they can be used for the reaction as the mixture thereof.

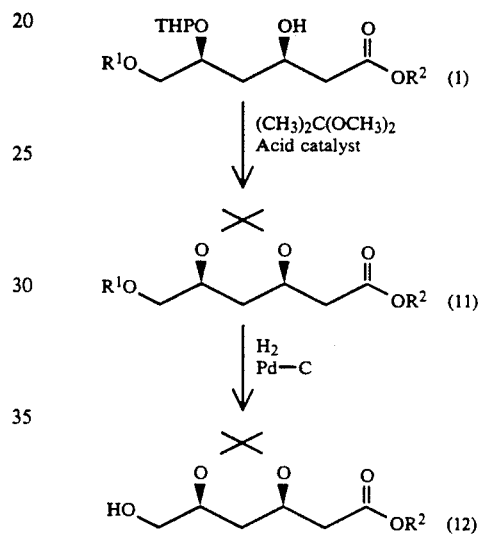

(in the above formulae, R$_1$, R$_2$, and THP have the same meaning as described above.)

EXAMPLES

The following examples are intended to illustrate the present invention practically but not to limit it any way.

In addition, the analyses in the examples were carried out using the following analytical instruments.

Molecular Structure

Infrared Absorption Spectrum (IR): Type IR-810 (trade name, made by JASCO Inc.)

Nuclear Magnetic Resonance Spectrum (NMR): Type AM-400 (400 MHz) (trade name, made by Bruker, Inc.)

Internal standard substance: Tetramethylsilane.

Optical Rotation: Type DIP-370 (trade name, manufactured by JASCO Inc.)

Optical Purity

High-Performance Liquid Chromatography: Hitachi Liquid Chromatography L-6000 (trade name, manufactured by Hitachi Ltd.)

Column: Cosmosil 5SL, $\phi$4.6 mm$\times$250 mm (trade name, manufactured by Nacalai Tesque Inc.)

Developing Solvent: Ether/hexane=1/9 by volume (1 ml/min.)

Detector: UV Detector L-4000 (UV-254 nm) (trade name, manufactured by Hitachi, Ltd.)

Gas Chromatography: 5890A (trade name, manufactured by Hewlett-Packard Company)

Column: Neutra Bond 1 (trade name, manufactured by GL Sciences Inc.)

Temperature: 100° to 250° C. (raised at 10° C./min.)

REFERENCE EXAMPLE 1

Production of Ethyl 4-Benzyloxyacetoacetate (8)

In a 500 ml reaction flask were placed 8.0 g (0.2 mol) of sodium hydride and 150 ml of tetrahydrofuran, and then 10.8 g (0.1 mol) of benzyl alcohol of formula (7) described above was added dropwise to the suspension at a temperature of from 40° to 50° C. under a nitrogen gas atmosphere. Thereafter, the resultant mixture was stirred for one hour and after adding dropwise 16.4 g (0.1 mol) of ethyl 4-chloroacetoacetate of formula (6) to the mixture, the reaction was carried out for 5 hours at room temperature. The reaction mixture obtained was added to 50 ml of ice-water and the product formed was extracted with 200 ml of toluene. After drying the organic layer (extract) obtained, toluene and tetrahydrofuran were distilled off and then the residue was distilled to provide 14.16 g (0.06 mol, percent yield 60%) of ethyl 4-benzyloxyacetoacetate of formula (8) described above as a colorless transparent liquid.

Boiling Point: 135° C./1 mmHg

IR(neat) cm.: 2975, 1740, 1730, 1660, 1500
$^1$H-NMR(CDCl$_3$):

δppm: 1.24(t,3H,J=7.2 Hz), 3.55(s,2H),
4.16(s,2H), 4.20(q,2H,J=7.2Hz),
4.55(s,2H), 7.33(aromatic,5H).

REFERENCE EXAMPLE 2

Production of Ethyl (S)-4-Benzyloxy-3-hydroxybutyrate (9)

In a 100 ml autoclave previously displaced with a nitrogen gas was placed 4.72 g (20.0 mmol) of ethyl 4-benzyloxyacetoacetate of formula (8) obtained in Reference Example 1 and after adding thereto a solution of 35 mg (0.02 mmol) of Ru$_2$Cl$_4$[(R)-Tol-BINAP]$_2$N(CH$_2$CH$_3$)$_3$ dissolved in 0.1 ml of methylene chloride together with 3.7 ml of ethanol, the enantioselective hydrogenation reaction was carried out under a hydrogen pressure of 10 to 11 kg/cm$^2$, and at a reaction temperature of 100° C. for 2 hours with stirring. After the reaction was over, the solvent was distilled off and the residue formed was distilled to provide 4.24 g (17.8 mmol, percent yield 89%) of ethyl (S)-4-benzyloxy-3-hydroxybutyrate of formula (9) described above.

Boiling Point: 124° C./0.3mmHg

[α]$_D^{25}$(c=1.1, CHCl$_3$:) −11.5°

IR(neat) cm$^{-1}$: 3450, 2975, 1740, 1500

$^1$H-NMR(CDCl$_3$):

δppm: 1.24(t,3H,J=7.1Hz),
2.55(d,2H,J=6.3Hz), 3.50(m,2H),
4.17(q,2H,J=7.1Hz), 4.24(m,1H),
4.68(s,2H), 7.32(aromatic, 5H)

The ethyl (S)-4-benzyloxy-3-hydroxybutyrate of formula (9) obtained in the above step was reacted with (R)-(+)-α-methoxy-α-trifluoromethylphenylacetic acid (hereinafter, is referred to as "MTPA") in methylene chloride in the presence of N,N'-dicyclohexylcarbodiimide and a catalytic amount of 4-dimethylaminopyridine to synthesize an MTPA ester form. As the result of analyzing the product by high-performance liquid chromatography (hereinafter, is referred to as "HPLC"), it was confirmed that the product was a mixture of 99.15% ethyl (S)-4-benzyloxy-3-hydroxybutyrate of formula (9) and 0.85% ethyl (R)-4-benzyloxy-3-hydroxybutyrate. Also, the optical purity of ethyl (S)-4-benzyloxy-3-hydroxybutyrate of formula (9) was 98.3% e.e.

REFERENCE EXAMPLE 3

Production of Ethyl (S)-4-Benzyloxy-3-tetrahydropyranyloxybutyrate (10)

To 4.0 g (16.7 mmol) of ethyl (S)-4-benzyloxy-3-hydroxybutyrate of formula (9) obtained in Reference Example 2 was added 20 ml of toluene and after further adding thereto 5 mg (26.3 mmol) of p-toluenesulfonic acid monohydrate, 1.6 g (19.0 mmol) of 3,4-dihydropyran was added dropwise to the mixture at room temperature followed by carrying out the reaction for 2 hours at the same temperature. The reaction mixture obtained was washed twice with 5 ml of an aqueous solution of sodium hydrogencarbonate and dried. After distilling off the solvent from the product, the residue was purified by silica gel column chromatography (developing solvent: hexane/ethylacetate=9/1 by volume) to provide 4.83 g (15.0 mol, percent yield 90%) of ethyl-(S)-4-benzyloxy-3-tetrahydropyranyloxybutyrate shown by formula (10) described above as a colorless transparent liquid.

IR(neat) cm$^{-1}$: 2940, 1735, 1500, 1030, 740, 700

$^1$H-NMR(CDCl$_3$):

δppm: 1.24(dt,3H,J=2.1Hz,7.2Hz),
1.43–1.84(m,6H), 2.62(m,2H),
3.46(m,1H), 3.54(d,1H,J=5.0Hz),
3.84(m,1H), 4.10(dq,2H,J=2.1Hz,7.2Hz),
4.30(m,1 H), 4.54(d,2H.J=2.1Hz),
4.78(m,1H), 7.32(aromatic,5H).

REFERENCE EXAMPLE 4

Production of Ethyl (S)-6-Benzyloxy-5-tetrahydropyranyloxy-3-oxohexanoate (2)

In 20 ml of methanol were dissolved 4.8 g (14.9 mmol) of ethyl (S)-4-benzyloxy-3-tetrahydroxypyranyloxybutyrate of formula (10) obtained in Reference Example 3 and 0.656 g (16.4 mmol) of sodium hydroxide and the solution was refluxed for 2 hours. After distilling off methanol from the reaction mixture, 20 ml of ice-water was added to the residue and the mixture was extracted with 30 ml of toluene. The aqueous layer was recovered and acidified with 1N sulfuric acid with cooling until pH became 6, the product was extracted with 50 ml of ethyl acetate. The organic layer (the extract) obtained was dried and concentrated, and the residue was purified by silica gel column chromatography (developing solvent: hexane/ethyl acetate=95/5 by volume) to provide 4.12 g (14.0 mmol, percent yield 94%) of (S)-4-benzyloxy-3-tetrahydropyranyloxybutyric acid as a light yellow transparent liquid.

IR(neat) cm$^{-1}$: 3400–3500, 2950, 1715, 1600

Then, 4.0 g (13.6 mmol) of (S)-4-benzyloxy-3-tetrahydropyranyloxybutyric acid obtained was dissolved in 30 ml of tetrahydrofuran and then 2.75 g (16.9 mmol) of 1,1'-carbonyldiimidazole was added to the solution at −15° C. Then, the mixture was stirred for one hour to increase a temperature to room temperature. The mixture was added dropwise to a suspension of 2.80 g (29 mmol) of magnesium chloride, 2.9 g (29 mmol) of triethylamine, and 4.22 g (25 mmol) of potassium ethyl malonate in 30 ml of tetrahydrofuran and the reaction was carried out for 6 hours at room temperature.

The reaction mixture obtained was concentrated and after adding thereto 1 N sulfuric acid until pH became 6 while cooling with the addition of 20 ml of ice-water, the product was extracted with 50 ml of ethyl acetate. The organic layer (the extract) was recovered, dried, and concentrated. The residue formed was purified by silica gel column chromatography (developing solvent: hexane/ethyl acetate=9/1 by volume) to provide 3.80 g (10.43 mmol) of ethyl (S)-6-benzyloxy-5-tetrahydropyranyloxy-3-oxohexanoate of formula (2) described above as a colorless transparent liquid with a percent yield of 70% from ethyl (S)-4-benzyloxy-3-tetrahydropyranyloxybutyrate of formula (10).

IR(neat) cm$^{-1}$: 2950, 1740–1720, 1650, 1500, 1150
$^1$H-NMR(CDCl$_3$):
δppm: 1.26(t,3H,J=7.2Hz), 1.50–1.80(br,6H),
2.80(m,2H), 3.45–3,5(m,4H),
4.26(q,2H,J=7.2Hz), 4.52(s,2H),
7.34(aromatic,5H).

REFERENCE EXAMPLE 5

Production of tert-Butyl (S)-6-Benzyloxy-5-tetrahydropyranyloxy-3-oxohexanoate (2)

In a 200 ml reaction flask was placed 40 ml of tetrahydrofuran and after cooling the flask in ice-water to 0° C., 60 ml of a n-hexane solution of 1.6M of lithium diisopropylamide was added thereto and further a solution of 11.06 g (95.4 mmol) of tert-butyl acetate dissolved in 10 ml of tetrahydrofuran was added dropwise to the mixture. Thereafter, the resultant mixture was stirred for 30 minutes, and after cooling the reaction mixture to −20° C., a solution of 12.3 g (33.8 mmol) of ethyl (S)-6-benzyloxy-5-tetrahydropyranyloxy-3-oxohexanoate of formula (2) dissolved in 20 ml of a tetrahydrofuran solution was added dropwise to the reaction mixture. Thereafter, the resultant mixture was stirred for one hour, the reaction mixture was poured into 100 ml of a saturated aqueous solution of ammonium chloride and the product was extracted with ethyl acetate. After drying the organic layer (the extract) obtained, the solvent was distilled off and the residue formed was purified by silica gel column chromatography (developing solvent: hexane/ethyl acetate=95/5 by volume) to provide 9.46 g (24.1 mmol, percent yield 71%) of tert-butyl (S)-6-benzyloxy-5-tetrahydropyranyloxy-3-oxohexanoate of formula (2) as a light-yellow transparent liquid.

IR(neat) cm$^{-1}$: 2950, 1740–1650, 1500, 1150
$^1$H-NMR(CDCl$_3$):
δppm: 1.47(9H), 1.50–1.80(6H), 2.80(m,2H),
3.45–3.5(m,4H), 4.52(s,2H),
7.34(aromatic,5H)

EXAMPLE 1

Production of Ethyl (3R,5S)-6-Benzyloxy-3-hydroxy-5-tetrahydropyranyloxyhexanoate (1)

After dissolving 1.0 g (2.75 mmol) of ethyl (S)-6-benzyloxy-5-tetrahydropyranyloxy-3-oxohexanoate of formula (2) obtained in Reference Example 4 in 2.0 ml of ethanol, the solution thus formed was placed in a 100 ml autoclave previously displaced with a nitrogen gas. Then, after adding thereto a solution of 2.3 mg (0.0013 mmol) of Ru$_2$Cl$_4$[(R)-Tol-BINAP]$_2$N(CH$_2$CH$_3$)$_3$ of formula (3) dissolved in 0.1 ml of methylene chloride, the enantioselective hydrogenation reaction was carried out for 18 hours with stirring under a hydrogen pressure of 30 kg/cm$^2$ and at a reaction temperature of 35° C.

After the reaction was over, the solvent was recovered and the residue formed was purified by silica gel column chromatography (developing solvent: n-hexane/ethyl acetate=85/15 by volume) while simultaneously removing the catalyst to provide 320 mg (0.87 mmol, percent yield 32%) of ethyl (3R,5S)-6-benzyloxy-3-hydroxy-5-tetahydrpyranyloxyhexanoate shown by formula (1) described above as a colorless transparent liquid.

IR(neat) cm$^{-1}$: 3450, 2940, 1730, 1600, 1100, 740, 700
$^1$H-NMR(CDCl$_3$):
δppm: 1.28(t,3H,J=7.2Hz), 1.60–1.80(m,6H),
2.40(m,2H), 3.40(t,2H,J=5.6Hz),
3.50(m,2H), 3.65(m,1H), 4.18(m.2H),
4.25(q,2H,J=7.2Hz), 4.54(s,2H),
7.32(aromatic,5H).

Then, ethyl (3R,5S)-6-benzyloxy-3-hydroxy-5-tetrahydropyranyloxyhexanoate of formula (1) thus obtained was reacted with MTPA to form an ester form as in Reference Example 2 and as the result of analyzing by HPLC, it was confirmed that the optical purity of the product was higher than 99% ee.

In addition, during the purification of ethyl (3R,5S)-6-benzyloxy-3-hydroxy-5-tetrahydropyranyloxyhexanoate, 209 mg (0.75 mmol, percent yield 27%) of ethyl (3R,5S)-6-benzyloxy-3,5-dihydroxyhexanoate without having the tetrahydropyranyl group as the protective group for the hydroxy group at the 5-position was obtained as a white crystal and the total yield of the foregoing compound and ethyl (3R,5S)-6-benzyloxy-3-hydroxy-5-tetrahydropyranyloxyhexanoate of formula (1) was 59%.

Melting Point: 34°–35 ° C.
IR(KBr) cm$^{-1}$: 3400, 2900, 1720, 1600, 735, 700
$^1$H-NMR(CDCl$_3$):
δppm: 1.26 (t,3H,J=7.2 Hz), 1.65 (m,2H),
2.46 (m,2H), 3.40 (m,2H), 4.08 (m,1H),
4.18 (q,2H,J=7.2 Hz), 4.29 (m,1H),
4.55 (s,2H), 7.32(aromatic,5H).

When ethyl (3R,5S)-6-benzyloxy-3,5-dihydroxyhexanoate thus obtained was reacted with acetone dimethylacetal to form isopropylidene acetal and as the result of analyzing by gas chromatography, it was confirmed that the formation ratio of the syn-diol form/the anti-diol form was 99/1 by weight and the selectivity for the syn-diol form was 98% d.e.

Also, when ethyl (3R,5S)-6-benzyloxy-3,5-dihydroxyhexanoate was recrystallized from ethanol and the analysis was carried out by the same manner as above, it was confirmed that the formation ratio of the syn-diol form/the anti-diol form was 99.4/0.6 by weight and the selectivity for the syn-diol form was 98.8% d.e.

In addition, for the sake of comparison, the compound, ethyl (3R,5S)-6-benzyloxy-5-tert-butyldimethylsilyloxy-3-hydroxyhexanoate wherein a tert-butyldimethylsilyl group, which was a conventionally known 3-substituted silyl group, was introduced in place of the tetrahydropyranyl group as the protective group for the hydroxy group at the 5-position in foregoing formula (1) was synthesized.

That is, when the foregoing enantioselective hydrogenation was carried out by the same reaction conditions as above except that ethyl (S)-6-benzyloxy-5-tert-butyldimethylsilyloxy-3-oxohexanoate was used in place of ethyl (S)-6-benzyloxy-5-tetrahydropyranyloxy-3-oxohexanoate of formula (2), a mixture of ethyl (3R,5S)-6-benzyloxy-5-tert-butyldimethylsilyloxy-3-hydroxyhexanoate and ethyl (3R,5S)-6-benzyloxy-3,5-dihydroxyhexanoate without having the tert-butyldimethylsilyl group was obtained. The product mixture was induced to isopropylidene acetal as described above and as the result of analyzing by gas chromatography, it was confirmed that the formation ratio of the syn-diol form/the anti-diol form was 96/4 by weight and the selectivity for the syn-diol form was 92% d.e.

From the foregoing results, it can be seen that when the reactions are carried out under the same conditions, the compound of the present invention is obtained at about 6% higher selectivity in the diasteromer excessive ratio than the case of the compound having introduced thereto the conventional protective group. The difference in the selectivity for the syn-diol form means that the compound of the present invention is excellent, particularly, in the synthesis of a medicament.

In addition, ethyl (S)-6-benzyloxy-5-tert-butyldimethylsilyloxy-3-oxohexanoate described above was obtained as follows.

That is, ethyl (S)-4-benzyloxy-3-hydroxybutyrate of formula (9) obtained in Reference Example 2 was reacted with tert-butyldimethylsilyl chloride in a mixed solvent of ethyl acetate and toluene at 1:1 by volume in the presence of 1 equivalent of imidazole and a catalytic amount of 4-dimethylaminopyridine to provide ethyl (S)-4-benzyloxy-3-tert-butyldimethyl-silyloxyacetate, and then by increasing two carbon atoms according to the method described in Reference Example 4, desired ethyl (S)-6-benzyloxy-5-tert-butyldimethylsilyloxy-3-oxohexanoate was obtained.

EXAMPLE 2

Production of tert-butyl (3R,5S)-6-benzyloxy-3-hydroxy-5-tetrahydropyranyloxyhexanoate (1)

In 2.0 ml of methanol was dissolved 1.0 g (2.55 mmol) of tert-butyl (S)-6-benzyloxy-3-oxo-5-tetrahydropyranyloxyhexanoate of formula (2) obtained in Reference Example 5 and the enantioselective hydrogenation reaction was carried out as in Example 1 using $Ru_2Cl_4[(R)-Tol-BINAP]_2N(CH_2CH_3)_3$ of formula (3) for 18 hours with stirring under a hydrogen pressure of 30 kg/cm$^2$ and at a reaction temperature of from 35° to 40° C. After the reaction was over, the solvent was recovered and the residue formed was purified by silica gel column chromatography (developing solvent: n-hexane/ethyl acetate 85/15 by volume) to provide 350 mg (0.89 mmol, percent yield 35%) of tert-butyl (3R,5S)-6-benzyloxy-3-hydroxy-5-tetahydropyranyloxyhexanoate of formula (1) as a colorless transparent liquid.

IR(neat) cm$^{-1}$: 3450, 2950, 1730, 1600, 1100, 740, 700
$^1$H-NMR(CDCl$_3$):
δppm: 1.60(s,9H), 1.60–1.80(m,6H),
2.40(m,2H), 3.40(t,2H,J=5.6Hz),
3.50(m,2H), 3.65(m,1H), 4.18(m,2H),
4.54(s,2H), 7.32(aromatic,5H).

Then, tert-butyl (3R,5S)-6-benzyloxy-3-hydroxy-5-tetrahydropyranyloxyhexanoate of formula (1) obtained was reacted with MTPA to form an ester form as in Reference Example 2 and as the result of analyzing by HPLC, it was confirmed that the optical purity of the product was higher than 95% e.e.

In addition, during the purification of tert-butyl (3R,5S)-6-benzyloxy-3-hydroxy-5-tetrahydropyranyloxyhexanoate, 280 mg (0.90 mmol, percent yield 35%) of tert-butyl (3R,5S)-6-benzyloxy-3,5-dihydroxyhexanoate without having the tetrahydropyranyl group as the protective group for the hydroxy group at the 5-position was obtained as a colorless transparent liquid and the total yield of the foregoing compound and tert-butyl (3R,5S )-6-benzyloxy-3-hydroxy-5-tetrahydropyranyloxyhexanoate, of formula (1) was 70%.

IR(neat) cm$^{-1}$: 3450, 2900, 1720, 1600, 735, 700
$^1$H-NMR(CDCl$_3$):
δppm: 1.60(br,9H), 1.65(m,2H), 2.45(m,2H),
3.40(m,2H), 4.08(m,1H), 4.29(m,1 H),
4. 55(s,2H), 7.32(aromatic,5H).

When tert-butyl (3R,5S)-6-benzyloxy-3,5-dihydroxyhexanoate obtained was reacted with acetone dimethyl acetal to form isopropylidene acetal and as the result of analyzing by gas chromatography, it was confirmed that the formation ratio of the syn-diol form/the anti-diol form was 91/9 by weight and the selectivity for the syn-diol form was 82% d.e.

EXAMPLE 3

Production of tert-butyl (3R,5S)-6-benzyloxy-3-hydroxy-5-tetrahydropyranyloxyhexanoate (1)

In 4.0 ml of tert-butyl alcohol was dissolved 2.0 g (5.10 mmol) of tert-butyl (S)-6-benzyloxy-3-oxo-5-tetrahydropyranyloxyhexanoate of formula (2) obtained in Reference Example 5 and the solution was placed in a 100 ml autoclave previously displaced with a nitrogen gas. Then, after adding thereto a solution of 4.6 mg (0.0026 mmol) of $Ru_2Cl_4[(R)-Tol-BINAP]_2N(CH_2CH_3)_3$ of formula (3) dissolved in 0.15 ml of methylene chloride, the enantioselective hydrogenation reaction was carried out for 18 hours with stirring under a hydrogen pressure of 30 kg/cm$^2$ and at a reaction temperature of 45° C. The conversion of reaction was 95%.

After the reaction was over, the solvent was recovered and the residue was purified by silica gel column chromatography (developing solvent: n-hexane/ethyl acetate=85/15 by volume) while simultaneously removing the catalyst to provide 1.2 g (3.05 mmol, percent yield 60%) of tert-butyl (3R,5S)-6-benzyloxy-3-hydroxy-5-tetrahydropyranyloxyhexanoate of formula (1) described above as a colorless transparent liquid.

Then, tert-butyl (3R,5S)-6-benzyloxy-3-hydroxy-5-tetrahydropyranyloxyhexanoate of formula (1) obtained was reacted with acetone dimethyl acetal to form isopropylidene acetal and as the result of analyzing by gas chromatography, it was confirmed that the formation ratio of the syn-diol form/the anti-diol form was 90/10 by weight and the selectivity of the syn-diol form was 80% d.e.

As described above, according to the present invention, the (3R,5S)-3,5,6-trihydroxyhexanoic acid derivative which is a useful compound capable of being easily converted into a lactone moiety, which is the active part of an inhibitor on HMG-CoA reductase, can be easily and efficiently obtained under a mild reaction condition with a high selectivity for the syndiol form.

While the invention has been described in detail and with reference to specific embodiments thereof, it will be apparent to one skilled in the art that various changes and modifications can be made therein without departing from the spirit and scope thereof.

What is claimed is:

1. A method of producing a (3R,5S)-3,5,6-trihydroxyhexanoic acid derivative represented by formula (1)

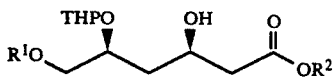 (1)

wherein R¹ represents a tert-butyl group or a benzyl group; R² represents a lower alkyl group; and THP represents a tetrahydropyranyl group, which comprises the step of enantioselectively hydrogenating an (S)-5,6-dihydroxy-3-oxohexanoic acid derivative represented by formula (2)

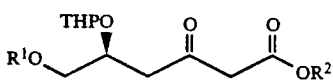 (2)

wherein R¹, R², and THP have the same meaning as described above, with a ruthenium-optically active phosphine complex represented by formula (3) as a catalyst $$Ru_2X_4[(R)-R^3-BINAP]_2N(CH_2CH_3)_3 \qquad (3)$$

[wherein R³-BINAP represents a tertiary phosphine represented by formula (4)

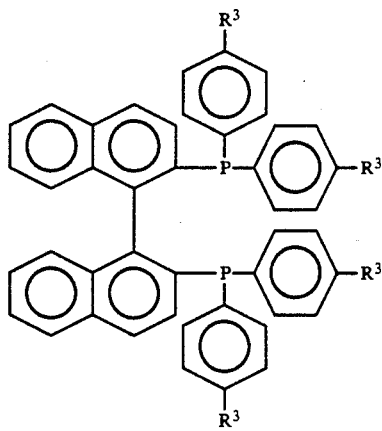 (4)

wherein R³ represents a hydrogen atom or a lower alkyl group; and X represents a chlorine atom or a bromine atom.

* * * * *